United States Patent [19]

Woods

[11] E Re. 29,641

[45] Reissued May 23, 1978

[54] MOIST HEATING PAD

[75] Inventor: Thomas G. Woods, Battle Creek, Mich.

[73] Assignee: Battle Creek Equipment Company, Battle Creek, Mich.

[21] Appl. No.: 713,691

[22] Filed: Aug. 12, 1976

Related U.S. Patent Documents

Reissue of:

[64] Patent No.: 3,889,101
Issued: Jun. 10, 1975
Appl. No.: 514,633
Filed: Oct. 15, 1974

[51] Int. Cl.[2] ..... H05B 3/36

[52] U.S. Cl. ..... 219/527; 128/256; 128/399; 219/529; 219/530; 219/549; 219/212

[58] Field of Search ..... 128/254, 256, 399; 219/211, 212, 527, 528, 529, 530, 540, 545, 546, 547, 549

[56] References Cited

U.S. PATENT DOCUMENTS

| | | | |
|---|---|---|---|
| 774,623 | 11/1904 | Wales | 219/212 |
| 1,653,901 | 12/1927 | Haessly | 128/256 |
| 1,754,763 | 4/1930 | Nunnally | 219/527 X |
| 2,154,184 | 4/1939 | Roberts | 219/528 |
| 2,215,042 | 9/1940 | Howard et al. | 219/529 |
| 2,393,182 | 1/1946 | Newell | 219/212 |
| 2,590,212 | 3/1952 | Samuels | 128/254 |
| 2,627,018 | 1/1953 | Duren | 219/527 |
| 2,633,846 | 4/1953 | Wray | 128/256 |
| 3,119,926 | 1/1964 | Mills et al. | 219/212 |
| 3,425,567 | 1/1969 | Mills | 219/212 |

*Primary Examiner*—Volodymyr Y. Mayewsky
*Attorney, Agent, or Firm*—Fisher, Gerhardt & Groh

[57] ABSTRACT

An improved heating device such as a heating pad comprising a fabric base and insulated resistance wire mounted in said pad, preferably in a backward and forward sinuous pattern, at least one thermostat connected in series with the resistance wire element at both ends by means of lead wires of a low resistance metal such as copper, each thermostat being positioned intimately with a span or straight portion forming part of a sinuous loop of resistance wire, a switch connected in series with the resistance wire, and a plurality of bars of a metal such as lead mounted in the pad. In an improved embodiment the insulation on the resistance wire is formed of a plastic material able to withstand the elevated temperatures attained by the resistance wire during operation.

11 Claims, 6 Drawing Figures

5.
21
25
18a
18a
21
27
28
47
16
41
42
20
5.

18a
17
44
27
25
18a
47
20
16
18
45
20
18

69
68
67
61
64
65
66
55
56
57
62
63
58
51
52
53
54
59
60

MOIST HEATING PAD

Matter enclosed in heavy brackets [ ] appears in the original patent but forms no part of this reissue specification; matter printed in italics indicates the additions made by reissue.

BACKGROUND OF THE INVENTION

1. Field of Invention

The present invention relates to electrically operated heating devices, and is more particularly concerned with such devices having a heating element mounted in a fabric, such as heating pads, blankets, clothing, and the like.

2. Prior Art

Heating pads disclosed in the prior art have been of several general forms. In one form, commonly known as the spiral construction form, a strand of resistance wire, commonly covered with asbestos insulation, has one end at the center of the pad fastened in place by sewing, and arranged in a spiral pattern, the spiral continuing until the pad reaches the desired size. In another form, the strand of resistance wire is in a sinuous pattern, running back and forth completely across the pad, or lengthwise of the pad, until sufficient elongated runs have been placed on the pad to give it the desired length. In both of these forms of construction, the standard practice is to sew the resistance wire in place between two piles of canvas or the like. This pattern interferes with uniform heating over the entire area of the heating pad and commonly causes what is termed "hot spots" in the pad. Pads made according to either of these forms are relatively satisfactory for some purpose, if used to supply low or moderate heat while lying flat, such as for the purpose of warming beds. However, where it is desired to supply heat to a surface or area that is not substantially level, these pads have not proved to be wholly satisfactory, largely due to their stiffness and rigidity with resulting inability to follow the contours of the surface to be heated. The difficulty involved, due to such stiffness and rigidity when the pad is in use, is normally referred to as "bridging."

Heat is commonly prescribed as a means of relieving congestion, pain, soreness, or injury. In order to apply heat effectively, the heat supplying mechanism must readily conform to the contour of the surface to be treated. This calls for a heating mechanism having a pliability and normally high temperature capability that has not been available or even possible in some of the prior art electric heating pads or blankets.

In U.S. Pat. No. 2,154,184, a heating pad is disclosed and claimed having a structure in which the heating element is in the form of small backward and forward sinous loops, several rows of loops being utilized to provide a heating element for the entire pad. Such structure is considerably more flexible than those previously disclosed and provided a pad which was sufficiently flexible to conform to the contours of the various parts of the body. Additionally, thermostats are incorporated in the pad and wired in series with the heating wire element. The thermostats are placed intermediate the rows of heating element loops. Although the heating element disclosed in the above-referred-to patent, constitutes a material improvement over the prior art devices, it still has several drawbacks in that there is a large temperature lag between the thermostat and the heating elements so that before the pad warms up sufficiently to provide suitable control by the thermostat, the temperature of the heating pad first rises to an undesirably high temperature. Additionally the asbestos insulation utilized for insulating the resistance wire often becomes unraveled or torn, resulting in the danger of short circuits and electric shocks.

SUMMARY OF THE INVENTION

Accordingly, it is an object of the present invention to produce a heating mechanism such as a pad, blanket or the like which is pliable in all directions and is able to fit the contours of parts of the body.

It is another object to provide a multi-screen heating mechanism wherein each section is formed of a series of relatively short turns or loops of an electrical resistance wire element such as nichrome wire.

It is still a further object to provide a heating mechanism wherein the sections are so mounted in parallel that they hinge at the point where one section is joined to the other.

It is an additional object to provide an electric heating pad which may be rolled or doubled up in use, or in storage, and yet which will not collapse, but will stay flat when unrolled or undoubled. It is an additional object to provide a heating pad for therapeutic use which will readily conform to the shape of the body on which it is to be used.

It is a further object of the invention to provide a heating pad which can provide moist heat without the need to first wet the fabric of the pad.

It is a prime object of the present invention to provide a heating pad having thermostats so arranged that they begin to operate and to maintain a uniform temperature without an initial cycle in which the temperature of the pad rises to a value considerably elevated over the desired temperature.

It is another object to provide a heating pad having resistance wire with an insulation which is strong and not subject to unraveling or tearing, and which remains undamaged at the elevated temperatures of operation of the pad.

It is another object to provide a heating pad of the type described having thermostats which are adequately encapsulated and protected.

Still further objects and advantages of the invention will appear from the description and drawings.

To the accomplishment of the foregoing and related ends, the invention comprises a heating pad formed of a fabric and having resistance wire element arranged having a suitable insulation covering and arranged in a plurality of rows each formed by a backward and forward sinuous looping of the element to provide flexibility of the pad. Additionally, one or more thermostats are connected in series with the resistance wire element on both sides by means of copper lead wires so that the thermostats may be placed within the loops of the element intermediate two adjacent strands of resistance wire or preferably directly adjacent a strand of wire, and thereby the more sensitive to the temperature of the element, and thereby avoiding the initial high temperature rise of the element before the thermostats are able to control the heating pad temperature.

DESCRIPTION OF THE PREFERRED EMBODIMENTS

Figure 1:
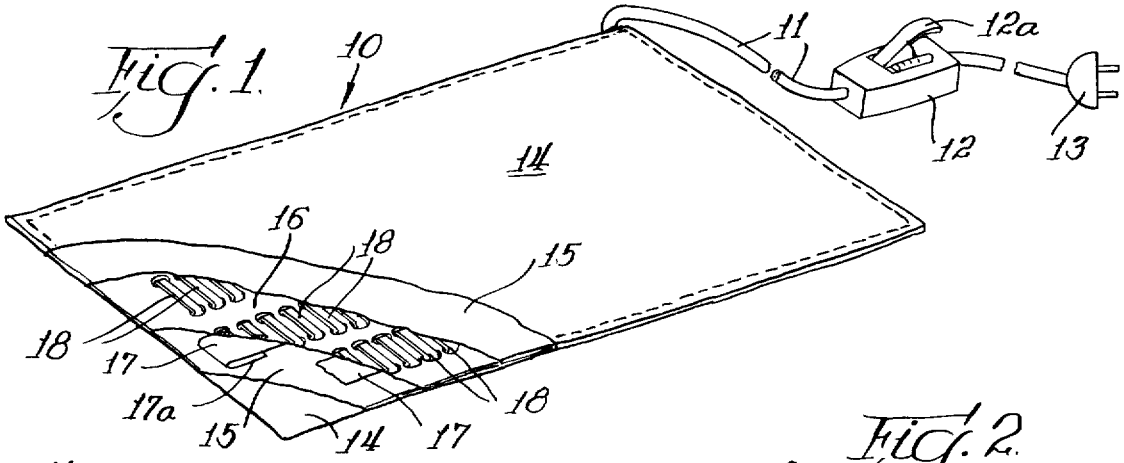
FIG. 1 is a perspective view, partly broken away, of a heating pad according to the invention.

Referring to FIGS. 1-4, a heating pad 10 according to the invention is shown comprising an electric line cord 11, a switch 12 in series therewith, and a plug 13 for plugging into a main socket. The switch 12 is preferably of the type which is spring-loaded normally open. When the operator desires to utilize the heating pad, he must press on the switch button 12a in order to close the switch. Current then flows as long as the button 12a is maintained in depressed position. When the hand is removed, the circuit is automatically opened. This provides protection to the operator in the event that he should fall asleep or fail to sense when the temperature of the pad becomes too high. The heating pad further comprises outer cover or bag 14 and inner cover or bag 15 of a canvas fabric conventionally known as "duck." Within the outer covers is an inner support sheet 16 also of duck material, and a plurality of strips 17 of duck material affixed thereto. The strips have end flaps 17a folded over at the ends. A plurality of strips or bars 18 of a metal such as a lead alloy are mounted on the support sheet 16 and have ends extending through apertures provided in the support sheet and have bent-over end portions 18a bent over the fabric strips 17. The metal strips 18 are formed of a lead alloy of such composition that it has a high [absorption] *adsorption* capability for water. Consequently, when the temperature of the heating pad is elevated as a result of electricity passing through the heating elements, moisture is driven off the lead strips and permeates the inner and outer coverings, providing moist heat to the area of the patient to which the pad is applied.

Figure 2:
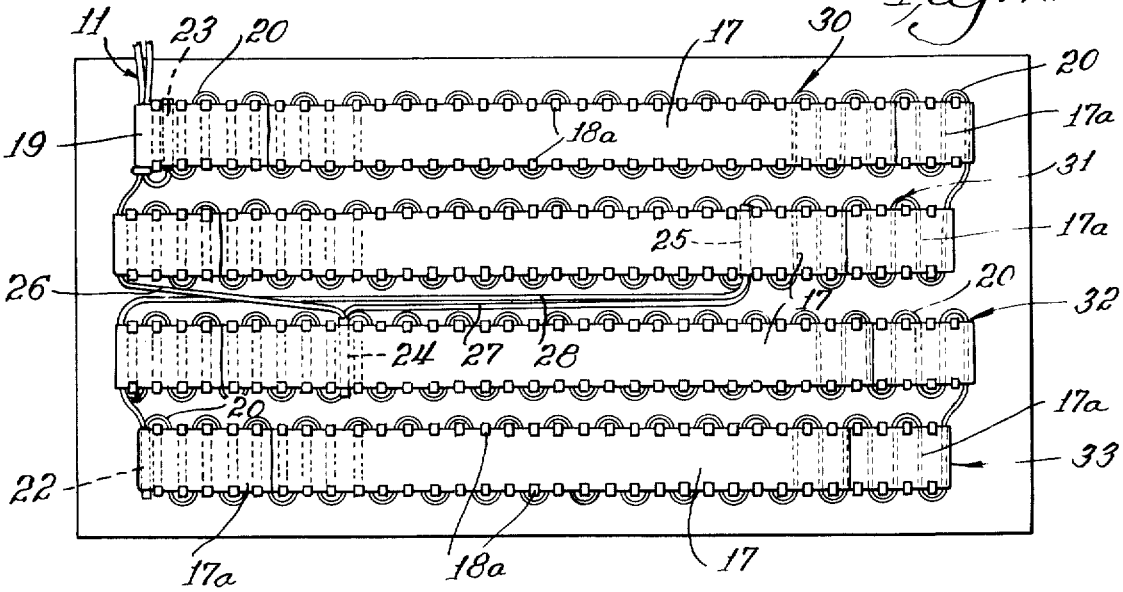
FIG. 2 is a plan view, partly broken away, of the heating pad shown in FIG. 1.
Figure 3:
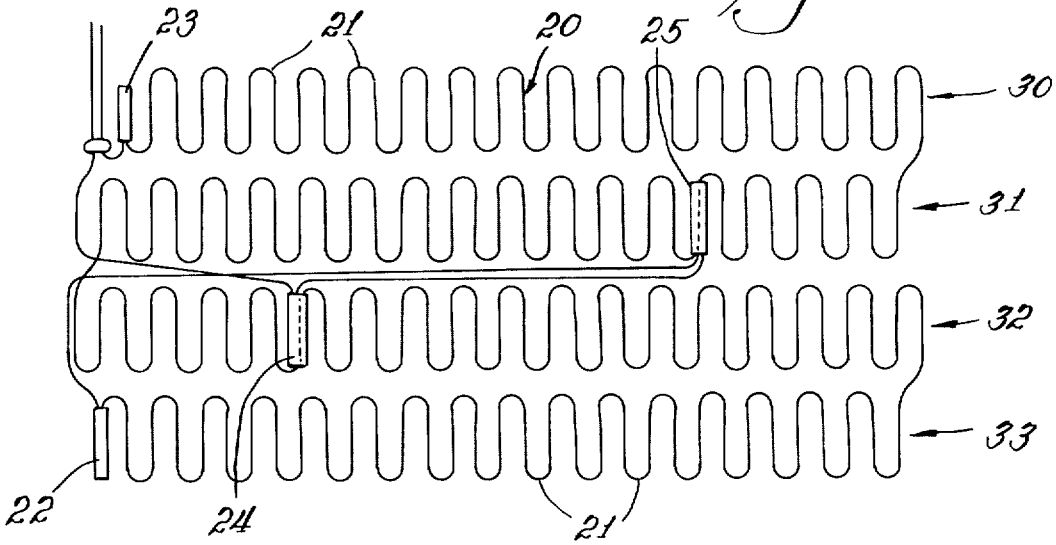
FIG. 3 is a plan view illustrating the circuitry of the resistance wire and thermostats.

As shown in FIG. 2, the line cord 11 enters the heating pad at a tubular line cord retainer 19. The heating element of the pad comprises insulated resistance wire 20 positioned in the form of a plurality of sinuous loops 21, shown in FIG. 3. As further shown in FIGS. 2 and 3, the line cord 11 is connected to the resistance wire by a connector 22. Copper lead wires 26, 27, and 28 connect thermostats 24 and 25 in series with each other and in series with the resistance wire. As shown in the drawings, the resistance wire is arranged in the form of banks of loops 30, 31, 32 and 33, disposed intermediate the support sheet 16 and the duck fabric strips 17. The duck strips 17 are affixed to the support sheet and maintained in position by the bent-over ends 18a of the lead strips 18. As shown in FIGS. 2 and 3, the thermostats are so placed that they are positioned directly over one of the two wires of a loop 21, and preferably in close proximity to one of the wires. Because of this arrangement, the temperature of the thermostat and the temperature of the resistance wire remain close together, generally within about 10°-15° F.

Figure 4:
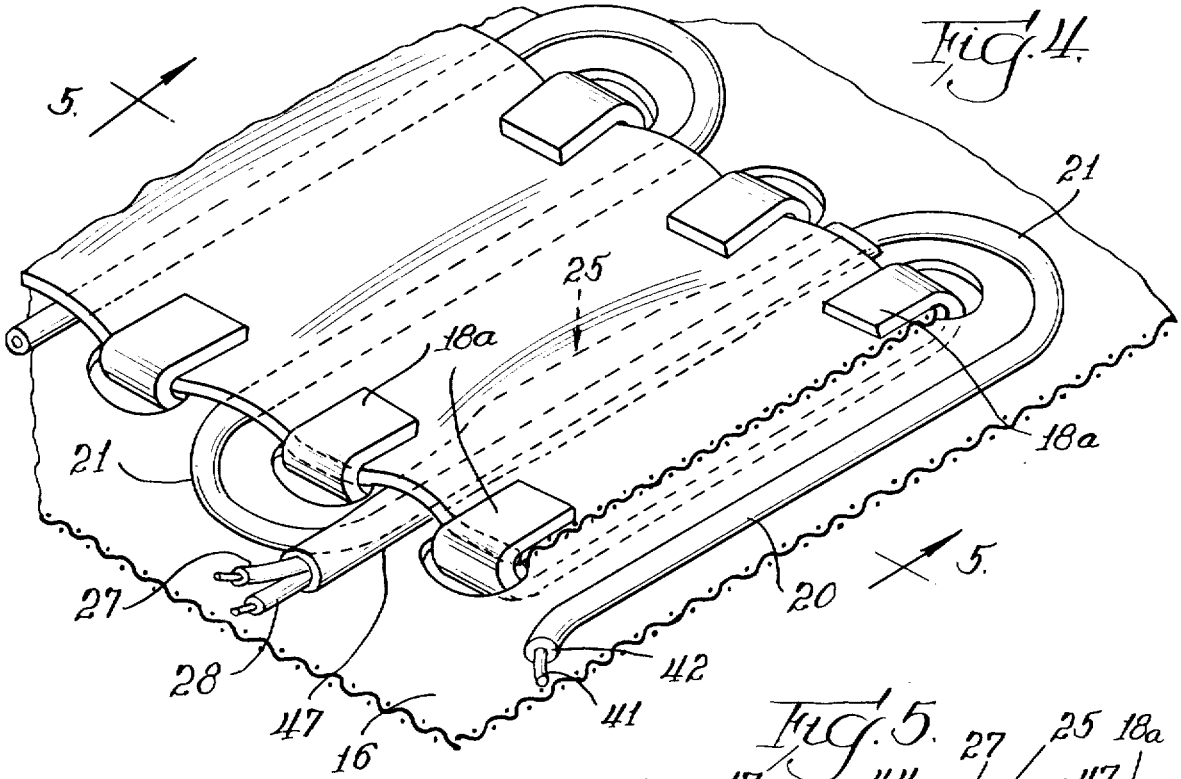
FIG. 4 is a fragmentary enlarged perspective view, partly broken away, of a portion of the heating pad shown in FIGS. 1-3.
Figure 5:
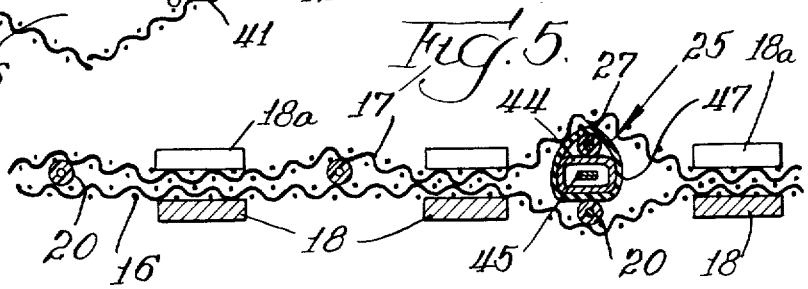
FIG. 5 is a fragmentary enlarged cross-sectional view taken at the line 5—5 of FIG. 4, looking in the direction of the arrows.

Referring to FIGS. 4 and 5, an enlarged portion of the heating pad surrounding the thermostat 25 is shown. Shown in the Figures are the resistance wire lead 20 comprising resistance wire 41 formed of nichrome or any other resistance heating wire generally known in the art. The wire 41 is covered with a plastic insulation sleeve 42 preferably formed of a material such as silicone rubber which has been found ideally suited for withstanding the temperatures attained by the resistance wire. Additionally, the material is tough and flexible and does not break or become cut over extended periods of use. The thermostat 25 is shown and comprises a conventional commercial tubular thermostat having an outer metallic jacket 44 and a conventional thermostat element 45 inside. A plastic heat-shrunk jacket 47 is positioned over the outer jacket 44 to protect the thermostat. Copper lead wires preferably having a silicone rubber insulating jacket are connected to the thermostat. The lead wires 27 and 28 are in turn connected in series with the electrical circuit. As shown, the thermostat is placed in the pocket formed between the support sheet 16 and the strip 17 which is held in place by the lead strip ends 18a. The resistance wire leads 20 are also disposed in the pocket and go down one pocket and up adjacent pockets. Consequently, the thermostat is positioned in close proximity to the heating wire line 20 and is directly heated along its entire length by the resistance wire. Consequently, only a small temperature lag develops when the electricity is first turned on to the heating pad.

Figure 6:
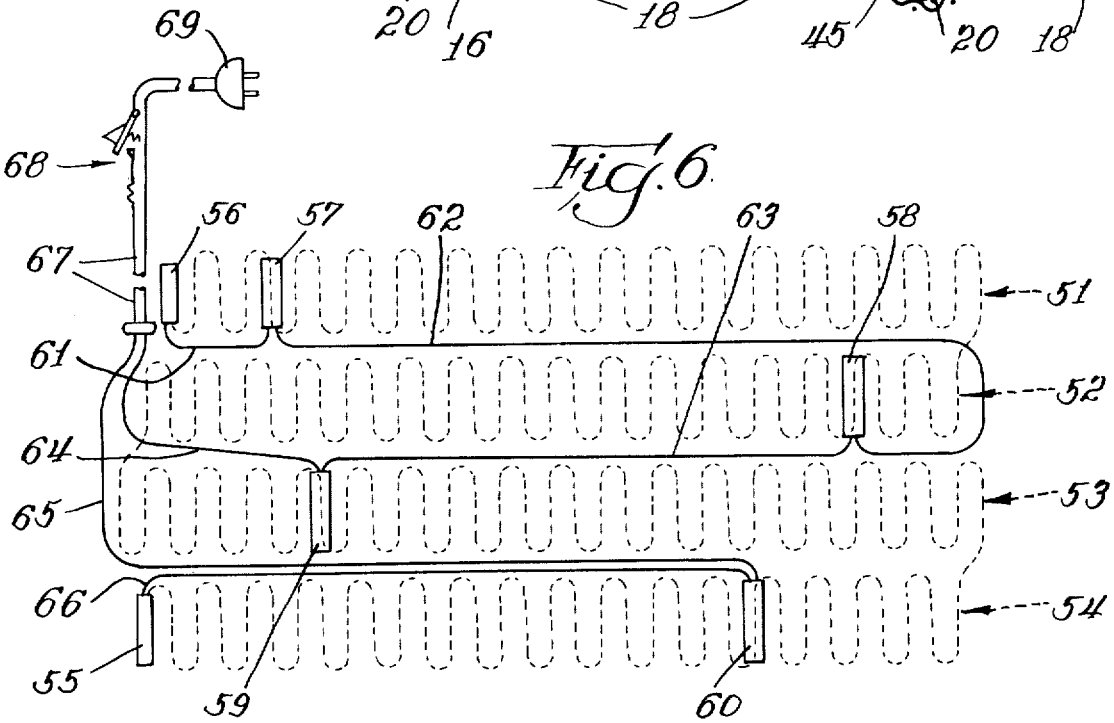
FIG. 6 is a plan view of the electrical portion of a heating pad in a modified embodiment.

In the heating pad shown in FIGS. 1-5, only two thermostats are utilized. However, for some applications, an in order to meet certain requirements of Underwriters Laboratory, a heating pad having a circuit as shown in FIG. 6 with four thermostats must be utilized. Shown diagramatically in FIG. 6 are banks of sinuous loops 51, 52, 53 and 54 of resistance wire similar to that shown and discussed above having a silicone rubber insulating jacket. Connectors 55 and 56 connect thermostats 57, 58, 59 and 60 to the resistance wire in the banks of loops 51-54 by means of insulated copper leads 61, 62, 63, 64, 65 and 66. A line cord 67 having a normally open spring switch 68 in series connects to the power main by means of a plug 69. The remaining structure of the heating pad is similar to that shown in FIGS. 1-5.

The heating pad of the present invention in its several embodiments has many advantages over those of the prior art. In the prior art pads asbestos was used as an insulation for the resistance wire and was applied to the wire generally by braiding. This had the advantage that it was easy to expose the face of the wire through movement. Moreover, if the asbestos was wound too tight, the heating element had a tendency to pop through. The asbestos-type insulated wire also posed a health problem since it contained asbestos fibers which are now becoming recognized as harmful to human beings. In the present heating pad the resistance wire is covered with a silicone rubber jacket which can withstand temperatures in excess of 500° F. Moreover, the material is so tough and resilient that it can bend without fracturing, and also is not readily cut on sharp surfaces.

The prior art pads also had a disadvantage in that they were directly connected in series with the resistance wire. As a result, they could not be mounted adjacent substantial lengths of resistance wire so that they could attain the temperature of the wire readily. Moreover, the actual contact of the thermostat with the heated resistance wire further contributed to poor tracking between the temperature of the heating element and the temperature of the thermostat. This tracking discrepancy generally shows up when the heating pad is first turned on. In the prior art heating pads, because of poor heat transfer between the heating element and the thermostat, the temperature of the heating element rises quickly and in the old heating pads rose to a value of about 60° F. above that of the thermostat before the thermostat could catch up. Because the present heating element has only a thin silicone rubber jacket, and since the thermostat is now connected to the heating system by separate copper leads, the thermostat can be mounted adjacent a substantial length of wire representing the length of a loop. As a result of this structure and materials, the heating element temperature even on the first cycle does not exceed a value 10°-15° above that of the thermostat. After the first cycle, the temperatures of the heating element and thermostat remain very close together, so that a uniform heating temperature is obtained.

It is to be understood that the invention is not to be limited to the exact details of operation or structures shown and described, as obvious modifications and equivalents will be apparent to one skilled in the art.

I claim:

1. A moist heating pad comprising:

a. a flexible moisture permeable base sheet, b. an electrical resistance wire heating element having an insulation sleeve mounted on said flexible base in a pattern comprising a plurality of substantially parallel banks of backward and forward sinuous loops having straight portions substantially perpendicular to the longitudinal direction of said banks, c. at least one thermostat encased in an insulation jacket connected in series with said heating element and connected at both of its ends by insulated lead wires of a highly conductive metal, said thermostat being positioned parallel and in close proximity to a straight portion of one loop of said heating element, d. a plurality of strips of a water [absorption] *adsorption* lead alloy mounted on said flexible base sheet each within one of said sinuous loops *said strips being heated by said heating elements to drive off adsorbed water,* e. an electrical line cord having a switch therein being electrically connected to said heating element, and f. a flexible moisture permeable cover enclosing said flexible base sheet, said heating element, said [• metal] strips and said thermostat.

2. A moist heating pad according to claim 1, wherein both the lead wires connected to said thermostat are of copper.

3. A moist heating pad according to claim 1, wherein said heating element is formed of nichrome wire.

4. A moist heating pad according to claim 1, wherein said insulation sleeve of said heater element is formed of silicone rubber.

5. A moist heating pad according to claim 1, wherein said thermostat is encased in a plastic heat-shrunk jacket.

6. A moist heating pad according to claim 5, wherein one of the lead wires connected to said thermostat is enclosed within said heat-shrunk jacket.

7. A moist heating pad according to claim 1, wherein said flexible base sheet is formed of fabric.

8. A moist heating pad according to claim 1, having a plurality of thermostats each similarly mounted.

9. A moist heating pad according to claim 1, having an inner cover within said outer cover, both of said covers being formed of fabric.

10. A moist heating pad according to claim 1, having a fabric strip covering each bank of sinuous loops, and affixed in place by turned-over ends of said [metal] strips.

*11. A moist heating pad comprising: a flexible moisture permeable base sheet, an electrical resistance wire heating element having an insulation sleeve mounted on said flexible base in a pattern of backward and forward sinuous loops, a thermostat having its opposite ends connected to insulated lead wires of a hightly conductive metal, said wire heating element and said insulated lead wires of said thermostat being connected together to connect said heating element and thermostat in series with an electric line cord, said thermostat being positioned in close proximity to a loop of said heating element, a plurality of flat lead alloy elements mounted on said flexible base sheet and uniformly within said sinuous loops, said flat lead alloy elements adsorbing water and being heated by said heating element to drive off adsorbed water, and a flexible moisture permeable cover enclosing said flexible base sheet, said heating element, said lead alloy elements and said thermostat.*

* * * * *